(12) United States Patent
Gonzalez et al.

(10) Patent No.: US 11,406,365 B2
(45) Date of Patent: Aug. 9, 2022

(54) NEEDLE HANDLE WITH VACUUM CHAMBER

(71) Applicant: Gyrus ACMI, Inc., Westborough, MA (US)

(72) Inventors: Hugo X. Gonzalez, Woodinville, WA (US); Sujeeth Parthiban, Bothell, WA (US); Chenhao Fu, Renton, WA (US); Michael S. Smith, Sammamish, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 271 days.

(21) Appl. No.: 16/496,004

(22) PCT Filed: Mar. 23, 2017

(86) PCT No.: PCT/US2017/023757
§ 371 (c)(1),
(2) Date: Sep. 20, 2019

(87) PCT Pub. No.: WO2018/174882
PCT Pub. Date: Sep. 27, 2018

(65) Prior Publication Data
US 2020/0100779 A1    Apr. 2, 2020

(51) Int. Cl.
*A61B 10/02* (2006.01)
*A61B 1/267* (2006.01)
*A61B 8/12* (2006.01)
*A61M 25/10* (2013.01)

(52) U.S. Cl.
CPC ........ *A61B 10/0283* (2013.01); *A61B 1/2676* (2013.01); *A61B 8/12* (2013.01); *A61M 25/10181* (2013.11); *A61M 25/10186* (2013.11); *A61B 10/0275* (2013.01); *A61B 2010/0208* (2013.01)

(58) Field of Classification Search
None
See application file for complete search history.

(56) References Cited

U.S. PATENT DOCUMENTS 4,668,215 A * 5/1987 Allgood .............. A61M 1/0062
                                              604/236
4,817,631 A * 4/1989 Schnepp-Pesch ..........................
                                              A61B 10/0283
                                              600/566
4,989,614 A * 2/1991 Dejter, Jr ........... A61B 10/0283
                                              600/565

(Continued)

*Primary Examiner* — Benjamin S Melhus
(74) *Attorney, Agent, or Firm* — Clements Bernard Baratta Walker; Michael S. Smith

(57) ABSTRACT

A device having a sheath, a medical device, a stylet, a handle having a chamber portion and a plunger device. The handle connects to proximal ends of the sheath, the medical device, and the stylet. The chamber portion includes a volume of space configured to volumetrically connect to at a lumen of the medical device, the sheath or the stylet. The plunger device slides and moves within the chamber portion. The plunger device is able to pneumatically or hydraulically isolate a proximal portion of the volume of space from a distal portion of the volume of space. Proximal movement of the stylet and the plunger device cause a suction effect (i.e., negative or reduced pressure) at the distal end of the sheath and/or the medical device.

20 Claims, 8 Drawing Sheets

(56) References Cited

U.S. PATENT DOCUMENTS

| | | | | |
|---|---|---|---|---|
| 5,060,658 A | * | 10/1991 | Dejter, Jr | A61B 10/0283 |
| | | | | 600/566 |
| 5,392,790 A | * | 2/1995 | Kanner | A61B 10/0283 |
| | | | | 600/566 |
| 6,273,861 B1 | * | 8/2001 | Bates | A61B 10/0275 |
| | | | | 600/567 |
| 2007/0106176 A1 | * | 5/2007 | Mark | A61B 10/0266 |
| | | | | 600/566 |
| 2007/0239064 A1 | * | 10/2007 | Cicenas | A61B 10/0275 |
| | | | | 600/566 |
| 2009/0082696 A1 | * | 3/2009 | Nicoson | A61B 10/0275 |
| | | | | 600/566 |
| 2011/0288437 A1 | * | 11/2011 | Ryan | A61B 10/0275 |
| | | | | 600/567 |
| 2012/0209140 A1 | * | 8/2012 | Ryan | A61B 10/06 |
| | | | | 600/564 |
| 2016/0081678 A1 | * | 3/2016 | Kappel | A61B 10/0233 |
| | | | | 600/567 |
| 2016/0262733 A1 | * | 9/2016 | Schlarb | A61B 10/0275 |
| 2020/0015796 A1 | * | 1/2020 | Van Liere | A61B 10/0275 |

\* cited by examiner

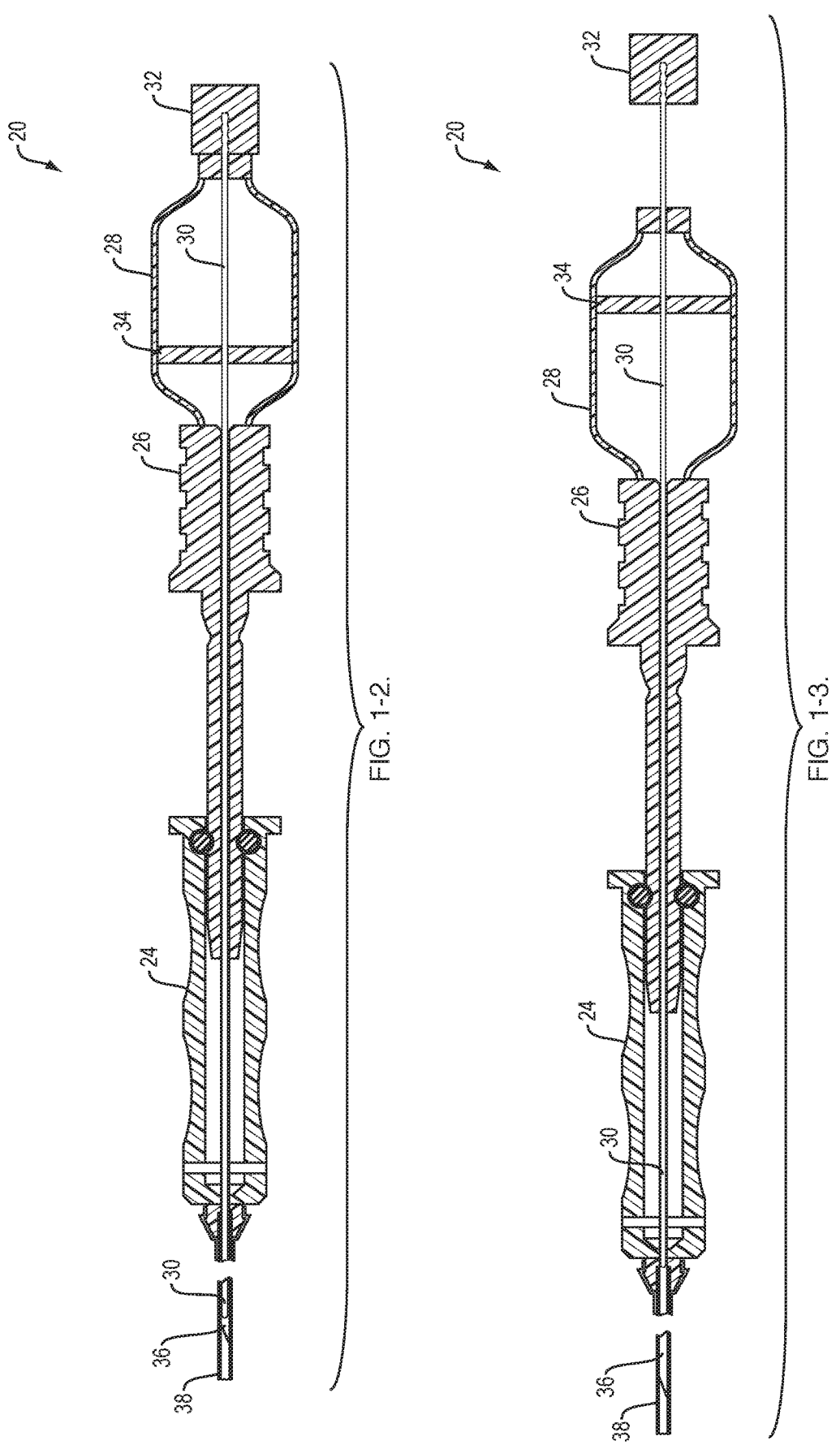

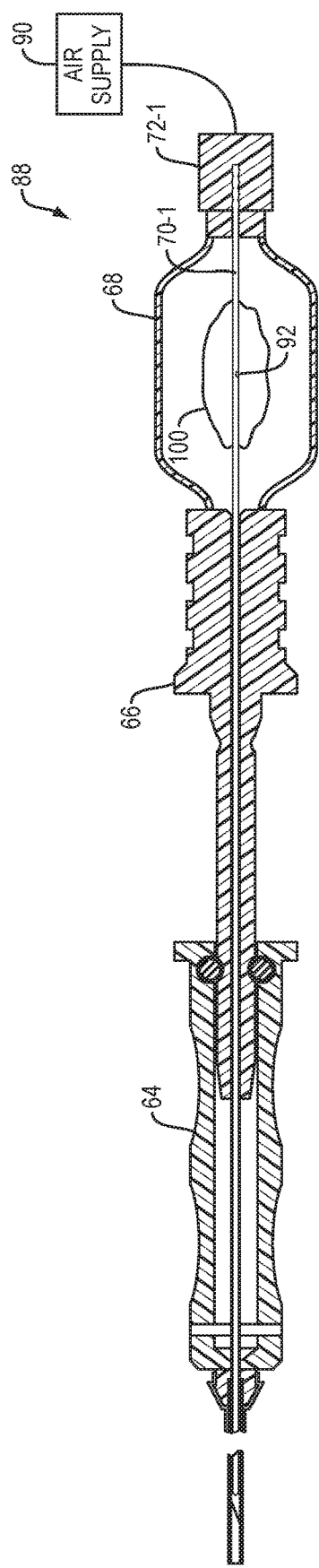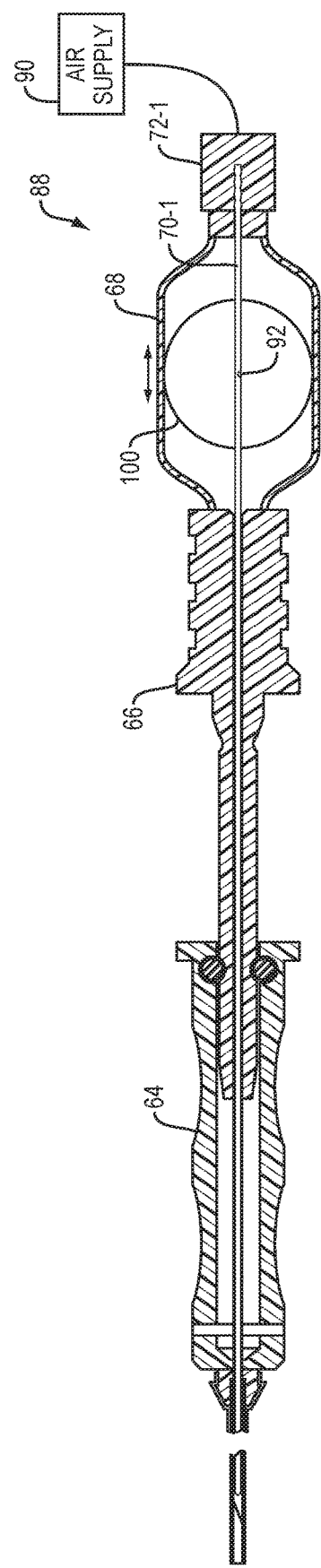

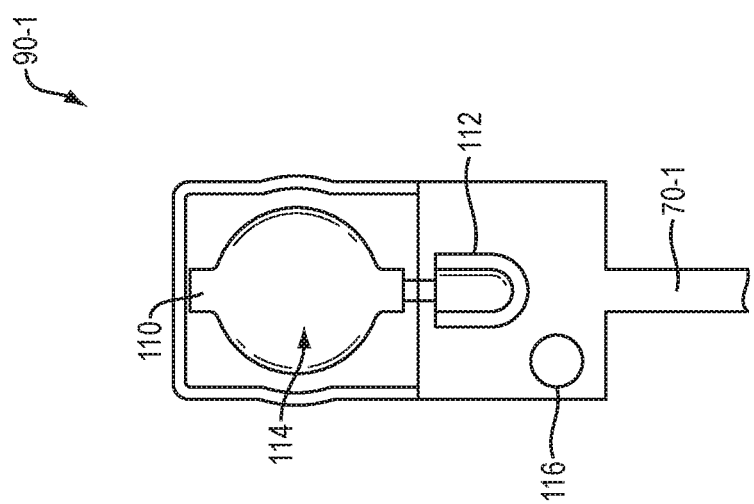

NEEDLE HANDLE WITH VACUUM CHAMBER

BACKGROUND

In procedures involving endobronchial ultrasound systems and transbronchial needle apparatus (i.e., sampling needle), a vacuum syringe is usually attached to the distal end of the sampling needle to aid in sample collection. To accomplish this, a stylet in the needle is removed first. Then after sampling, the stylet is reinserted before resampling. This adds procedural time, risk of contamination and risk of bending/kinking the components. To avoid this, some physicians slowly pull the stylet to generate some suction at the needle tip. However, bench experiments indicate that the amount of vacuum generated by stylet movement is very small and the vacuum is easily lost because the stylet is not sealed at the distal end.

SUMMARY

The present invention provides a device having a sheath, a medical device, a stylet, a handle and a plunger device. The handle includes a base portion connected to the proximal end of the sheath, an actuator connected to the proximal end of the medical device and a chamber portion connected to at least the actuator. The actuator includes a shaft portion that slides within the lumen of the base portion and a handle portion connected to the shaft portion. The shaft portion or the handle portion is connected to the proximal end of the medical device. The chamber portion includes a volume of space configured to volumetrically connect to at least one of the lumen of the medical device or the sheath and a plunger device configured to slide within the chamber portion and configured to pneumatically or hydraulically isolate a proximal portion of the volume of space from a distal portion of the volume of space. Proximal movement of the stylet and the plunder device cause a suction effect (i.e., reduced pressure) at the distal end of the sheath, the medical device and/or the stylet.

In one embodiment, the plunger device includes a plunger that is attached to the stylet and makes a seal with an interior wall of the chamber portion.

In another embodiment, the plunger device includes a plunger with a hole having a diameter dimension greater than a diameter dimension of the stylet and a tab attached to the stylet. The tab is located on a distal side of the plunger when the stylet is received through the hole within the chamber portion.

In still another embodiment, the stylet includes a lumen, a distal port and a proximal port. Proximal motion of the stylet causes reduced pressure at the distal end of the medical device, the sheath and/or the stylet due to the plunger moving as a result of the tab applying a proximal force to the plunger.

In yet another embodiment, a pneumatic or fluidic communication exists between a proximal portion of the volume of space and a distal portion of the volume of space when the tab is not in contact with the plunger.

In still yet another embodiment, the plunger device includes a second tab attached to the stylet. The second tab is located on a proximal side of the plunger when the stylet is received through the hole within the chamber portion.

In a further embodiment, a pneumatic or fluidic communication exists between a proximal portion of the volume of space and a distal portion of the volume of space when the first tab and the second tab are not in contact with the plunger.

In still further embodiments, the stylet further includes a port and a lumen that extends from a proximal end of the stylet to the port. The plunger device includes an inflatable balloon attached to the stylet around the port. The device further includes a gas or a fluid source that supplies a gas or a fluid into the inflatable balloon via the stylet lumen and the port. When the balloon is in an inflated state, a portion of an outer surface of the balloon makes at least one of a pneumatic or fluidic seal with an inner wall of the chamber portion.

BRIEF DESCRIPTION OF THE DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings:

FIG. 1-2 illustrates a cross-sectional view of the aspiration device of FIG. 1-1;

FIG. 1-3 illustrates a side view of the aspiration device of FIG. 1-1 in a second operational position;

FIG. 1-4 illustrates a cross-sectional view of the stylet of the aspiration device of FIG. 1-1;

FIG. 2-1 illustrates a cross-sectional view of an aspiration device formed in accordance with principles of the present invention;

FIG. 2-2 illustrates a cross-sectional view of the aspiration device of FIG. 2-1 in a second mode of operation;

FIG. 3-1 illustrates a cross-sectional view of an aspiration device formed in accordance with principles of the present invention;

FIG. 3-2 illustrates a cross-sectional view of the aspiration device of FIG. 3-1 in a second operational position;

FIG. 3-3 illustrates a cross-sectional view of the aspiration device of FIG. 3-1 in a third operational position;

FIG. 4-1 illustrates a cross-sectional view of an aspiration device formed in accordance with principles of the present invention;

FIG. 4-2 illustrates a cross-sectional view of the aspiration device of FIG. 4-1 in a second mode of operation; and FIG. 4-3 illustrates a pump mechanism to be incorporated with the device of FIGS. 4-1 and 4-2.

DETAILED DESCRIPTION

Figure 1:
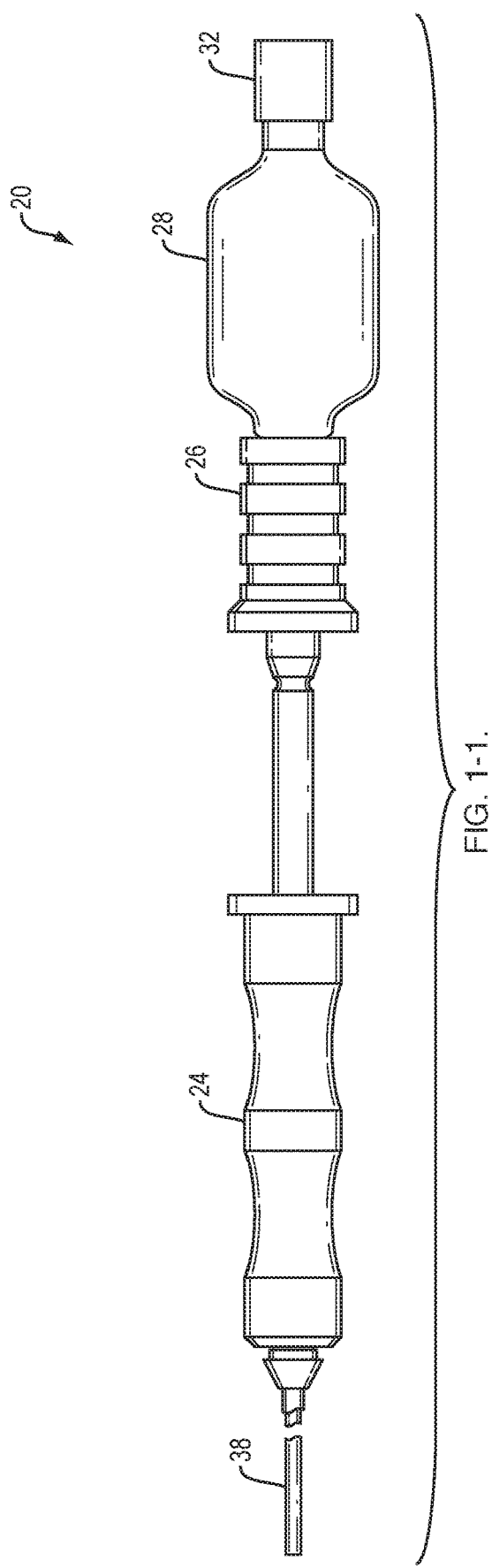
FIG. 1-1 illustrates a side view of an aspiration device formed in accordance with principles of the present invention.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the description herein, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description. The teachings herein may be used without limitation. In other words, the teachings herein may be used in any medical procedure. The teachings herein may be used for accessing any part of any anatomy. For example, one or more, or various vessels, passages, lumens, body cavities, tissue, organs, the like, or a combination thereof in humans and animals can be accessed using the teachings herein.

The teachings include a needle device for use in an endobronchial ultrasound (EBUS) system or in other delivery systems.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the description herein.

While the teachings herein refer to and reference terms like "bronchoscope", "lymph node", "nodule", "device", "needle", and the like, it is understood that these terms are broad, and the teachings herein can be used without limitation. In other words, the teachings herein may be suitable for illuminating other vessels, passages, lumens, body cavities, anatomy, tissue, organs, the like, or a combination thereof in humans and animals. One or more devices may function to control motion of a needle, needle sheath and/or catheter, thus improving navigation. The one or more devices may include one or more bronchoscopes.

The one or more bronchoscopes may be or may provide a device for attaching to a steerable catheter that can allow a user to sample tissue within or around human lumen. The one or more bronchoscopes may provide for insertion, manipulation, and operation of various surgical instruments in the anatomy of a patient. The one or more bronchoscopes may provide for delivery of the catheter into the anatomy. The one or more bronchoscopes may be used to visually inspect a site of interest, like the airways and lungs of a patient. The one or more bronchoscopes may be used to examine, treat, and/or diagnose lung growth, lung problems, lung cancer, lymph node(s), atelectasis, suspected interstitial lung disease, a lung rejection after a lung transplant, and/or to remove fluid or mucus plugs from the airways of a patient. The one or more bronchoscopes may be at least partially flexible, at least partially rigid, or both. The one or more bronchoscopes may include one or more ultrasound probes.

One or more catheters may function to provide a channel, a lumen, an opening, and/or a passageway for one or more devices to be advanced and/or introduced into the anatomy. The one or more catheters may function to introduce into the anatomy one or more medical devices, needles, transbronchial needle aspiration devices, cytology brushes, biopsy forceps, guiding devices, ultrasonic probes, illumination devices, therapies (i.e., chemotherapy, proteinomics, microspheres, etc.), fiducials, the like, or a combination thereof. The one or more catheters may be used to remove or expel from the anatomy one or more devices, fluids, tissue samples, abnormalities, foreign matter, or a combination thereof. The one or more catheters may each contain one or more lumen. The one or more catheters may include one or more sections that are generally rigid, one or more sections that are generally flexible, or a combination of both. The one or more catheters may include one or more sections that are generally rigid, generally flexible, or a combination of both. The one or more catheters may be at least partially flexible, bendable, articulable, or a combination thereof so that access to regions of interest can be easily obtained. The one or more catheters may bend or articulate 15 degrees or more, 45 degrees or more, 60 degrees or more, 90 degrees or more, 110 degrees or more, or even 130 degrees or more. The one or more catheters may be fabricated from a metal alloy, such as stainless steel or Nitinol (nickel and titanium at various percentages), a polymer, nylon, silicon, or any other suitable material. An outer surface of the one or more catheters may include a lubricant to facilitate insertion into, and removal from, the anatomy, the bronchoscope, a working channel of the bronchoscope, or a combination thereof. The one or more catheters may be elongated tubular members. The one or more catheters may extend along a longitudinal axis, a catheter axis, or both. The one or more catheters may include a uniform cross section, or the cross section may vary, taper, widen, narrow, or a combination thereof. The cross section of the one or more catheters may be circular, oval, irregular, and/or any other suitable shape or configuration. The cross section of the one or more catheters may be expandable, collapsible, formable, deformable, or a combination thereof. The one or more catheters may be configured to house, contain and/or protect any size or gauge needle with sheath. For example, the one or more catheters may house, contain, and/or protect about a 22 gauge needle or less, about a 21 gauge needle, about a 19 gauge needle or greater, etc. An outer surface of the one or more catheters may include one or more echogenic features or scribes. The one or more catheters may include one or more echogenic features so that the position and orientation of the catheter, the device, the needle, the needle tip, or a combination thereof can be viewed. The one or more catheters may include or define a hole or opening at a distal end, a proximal end, at a region in between, or a combination thereof so that one or more devices or instruments can pass therethrough. The one or more catheters may include or define an inner surface, an inner diameter, an inner portion, or a combination thereof that is dimensioned to generally conform to the outer diameter of the one or more needles or needle sheaths.

The one or more sheaths may function to be advanced into the anatomy for safe delivery of the one or more needles. The one or more sheaths may also function to provide medicine, therapy, or both to the anatomy. The one or more sheaths may also function to provide, develop, or have a local vacuum to a distal end or at a distal tip thereof. The one or more sheaths may be advanced towards and retracted from the region of interest via one or more catheters, devices, bronchoscopes, a handle, or a combination thereof. The one or more sheaths may be at least partially contained within the catheter. The one or more sheaths may be moved, advanced, retracted, or a combination thereof in the catheter. The one or more sheaths may have a length that extends along a longitudinal axis, a sheath axis, or both. The one or more sheaths may have a constant cross section, a varying cross section, a tapered cross section, an irregular cross section, or a combination thereof. The cross section of the one or more sheaths may be generally circular, oval, irregular, or any other suitable shape. The one or more sheaths may be generally hollow. The one or more sheaths may include a generally concentric outer diameter and inner diameter. The one or more sheaths may have an outer diameter and an inner diameter, one or more of which may have a constant size along a length of the sheath. The one or more sheaths may have an outer diameter and an inner diameter, one or more of which may vary, taper, slope, change, or a combination thereof. The one or more sheaths may be formed from a single material, or may be formed from one or more materials. The one or more sheaths may be fabricated from any material suitable for use in medical procedures. The one or more sheaths may be made of a polymer or other similar material. The one or more sheaths may be generally rigid, generally flexible, or both. The one or more sheaths may include one or more portions or sections that are generally rigid, one or more portions or sections that are generally flexible, or both. The one or more sheaths may be at least partially flexible, bendable, articulable, or a combination thereof so that access to regions of interest can be easily obtained. The one or more sheaths may bend or articulate about 15 degrees or more, about 45 degrees or more, about 60 degrees or more, about 0 degrees or more, about 110 degrees or more, or even about 130 degrees or more. The one or more sheaths may include one or more hypotubes. The one or more sheaths may be relatively smooth and able to freely slide, rotate, or otherwise move within a catheter, a bronchoscope, a device, the anatomy, or a combination thereof. The one or more sheaths may include one or more holes, ports, slots, apertures, openings, the like, or a combination thereof at the distal end, a proximal end, or a location therebetween. The one or more sheaths may include one or more holes, ports, slots, the like or a combination thereof for introducing medicine or therapy to the anatomy.

The one or more sheaths may be any size or gauge. That is, the one or more sheaths may be about 22 gauge or less, about 21 gauge, or about 19 gauge or greater, etc. The one or more sheaths may include a combination of two or more gauges. That is, for example, a proximal portion of the sheath may be about 21 gauge and a distal portion of the sheath may be about 19 gauge, or vice versa. The one or more sheaths may include two or more portions that are joined together fixedly, permanently, temporarily, or a combination thereof and those portions may have different memory shapes. The two or more portions may be the same gauge, or may be different gauges. The sheath may include one or more, or even two or more echogenic markings or scribes. The one or more echogenic features may function to enhance visibility. The one or more echogenic features may function to create one or more echogenic reflections during ultrasonic imaging so that a position or location of the sheath within the anatomy can be determined. The one or more echogenic features may be or may include one or more scribes, bands, slots, segments, shapes, surfaces, recesses, roughened surfaces, embedded material(s), coatings, grooves, serrations, notches, or a combination thereof. The one or more echogenic features may be one or more dimples, scallops, spiral scribes, helixes, squiggles, angled squiggles, jig-saws, symmetrical shapes, asymmetrical shapes, patterns, dots, dashes, lines, formations, or a combination thereof.

The one or more needles may function to be advanced into the anatomy to penetrate a site or region of interest. The one or more needles may function to puncture a region of interest so that the tissue sampling may occur. The one or more needles may also function to provide medicine, therapy, or both to the anatomy. The one or more needles may also function to provide, develop, or have a local vacuum to a distal end or at a distal tip thereof. The one or more needles may be advanced towards and retracted from the region of interest via one or more catheters, devices, bronchoscopes, a needle handle, or a combination thereof. The one or more needles within a sheath(s) may be at least partially contained within the catheter. The one or more needles may be moved, advanced, retracted, or a combination thereof in the catheter or in the sheath. The one or more needles may have a length that extends along a longitudinal axis, a needle axis, or both. The one or more needles may have a constant cross section, a varying cross section, a tapered cross section, an irregular cross section, or a combination thereof. The cross section of the one or more needles may be generally circular, oval, irregular, or any other suitable shape. The one or more needles may be generally hollow. The one or more needles may include a generally concentric outer diameter and inner diameter. The one or more needles may have an outer diameter and an inner diameter, one or more of which may have a constant size along a length of the needle or the sheath. The one or more needles may have an outer diameter and an inner diameter, one or more of which may vary, taper, slope, change, or a combination thereof. The one or more needles may be formed from a single material, or may be formed from one or more materials. The one or more needles may be fabricated from any material suitable for use in medical procedures. The one or more needles may be made from a metal or metal alloy, such as stainless steel, nitinol, or the like. The one or more needles may include a polymer or other suitable covering. The one or more needles may be generally rigid, generally flexible, or both. The one or more needles may include one or more portions or sections that are generally rigid, one or more portions or sections that are generally flexible, or both. The one or more needles may be at least partially flexible, bendable, articulable, or a combination thereof so that access to regions of interest can be easily obtained. The one or more needles may bend or articulate about 15 degrees or more, about 45 degrees or more, about 60 degrees or more, about 0 degrees or more, about 110 degrees or more, or even about 130 degrees or more. The one or more needles may be constructed from one or more hypotubes. The one or more needles may be constructed from one or more hypotubes that are relatively smooth and able to freely slide, rotate, or otherwise move within a catheter, a bronchoscope, a device, the anatomy, or a combination thereof. The one or more needles may include one or more holes, ports, slots, apertures, openings, the like, or a combination thereof at the distal end, a proximal end, or a location therebetween. The one or more needles may include one or more holes, ports, slots, the like or a combination thereof for tissue sample collection; for introducing a stylet into the needle; for introducing the stylet into the anatomy; for introducing medicine or therapy to the anatomy; or a combination thereof.

The one or more needles may be any size or gauge. That is, the one or more needles may be about 22 gauge or less, about 21 gauge, or about 19 gauge or greater, etc. The one or more needles may include a combination of two or more gauges. That is, for example, a proximal portion of the needle may be about 21 gauge and a distal portion of the needle may be about 19 gauge, or vice versa. The one or more needles may include two or more portions that are joined together fixedly, permanently, temporarily, or a combination thereof and those portions may have different memory shapes. The two or more portions may be the same gauge, or may be different gauges. One or both of the portions may include an interior size or region that is generally the same size as the one or more stylets. That is, the one or more stylets may substantially occupy some, most, or all of the interior of the one or more needles, needle portions, or both. One or both of the needle portions, the needle, or both may be slightly larger than the one or more stylets, so that the stylets only occupy some of the interior space or region of the one or more needles, needle portions, or both. The one or more needles may include an elongated section, member, or shaft and a distal tip or needle tip. The elongated section, the needle tip, or both may include one or more, or even two or more echogenic markings or scribes. The one or more echogenic features may function to enhance the visibility of the catheter, the needle, the needle tip, or a combination thereof. The one or more echogenic features may function to create one or more echogenic reflections during ultrasonic imaging so that a position or location of the catheter, the needle, and/or the needle tip within the anatomy can be determined. The one or more echogenic features may be or may include one or more scribes, bands, slots, segments, shapes, surfaces, recesses, roughened surfaces, embedded material(s), coatings, grooves, serrations, notches, or a combination thereof. The one or more echogenic features may be one or more dimples, scallops, spiral scribes, helixes, squiggles, angled squiggles, jig-saws, symmetrical shapes, asymmetrical shapes, patterns, dots, dashes, lines, formations, or a combination thereof. The one or more needles may include a distal tip.

The distal end of the needle, the distal tip, the needle tip, or a combination thereof may be configured to function as a piercing tip or feature so that cells, tissue, foreign matter, or a combination thereof can be obtained. The needle tip may be angled, sharply angled, beveled, flat, or a combination thereof so that tissue samples can be cut, cored, scraped from a site or region of interest. The needle tip may include a notched portion, a recessed portion, and/or a lancet tip or feature. A local vacuum may be created or formed at a distal end of the needle, a distal portion, or a needle tip so that tissue samples, foreign matter, or both can be aspirated or moved into the needle, the sample storage area, or both. The one or more needle tips and corresponding sheath may be contained within the one or more catheters as the catheter is advanced through the anatomy towards the site or region of interest. The one or more sheaths and the needle tips may be advanced or extended past a distal end of the one or more catheters when the catheter is near the region of interest. The one or more needle tips may be generally rigid, flexible, or both. The distal end, the needle tip, or both may include one or more echogenic features. The one or more needles may include one or more sample storage areas. An example needle is shown in PCT Application Ser. No. PCT/US16/20011 filed Feb. 29, 2016.

The one or more stylets may function to steer or guide the one or more needles, catheters, devices, or a combination thereof around the anatomy to the region of interest. The one or more stylets may be disposed within the needle such that the distal ends of the stylet and the needle are substantially aligned. The one or more stylets may function to block or prevent debris (i.e., tissue, blood, and the like) from entering the needle as the needle is advanced towards a site or region of interest. The one or more stylets may be formed from a single material, or may be formed from one or more materials. The one or more stylets may be fabricated from any suitable material. The one or more stylets may be made from a metal or metal alloy, such as stainless steel, nitinol, or the like. The one or more stylets may be formed from a shape memory material (i.e., metal or polymer). The one or more stylets may comprise a polymer or other suitable covering over at least a portion of the length of the stylets. The one or more stylets may be at least partially rigid, at least partially flexible, or both. The one or more stylets may include one or more portions (i.e., a distal portion, a proximal portion, or a portion in between) that are at least partially rigid, at least partially flexible, or both. The one or more stylets may be at least partially flexible, bendable, articulable, or a combination thereof so that the stylet can be positioned along a central lumen, opening, and/or interior portion of the needles. The one or more stylets may bend or articulate about 15 degrees or more, about 45 degrees or more, about 60 degrees or more, about 90 degrees or more, about 110 degrees or more, or even about 130 degrees or more. The one or more stylets may have a generally uniform cross section, or the cross section may be variable. At least a portion of the outer surface of the one or more stylets may be substantially the same size as the interior of one or more needle portions of the one or more needles so that the stylet substantially occupies some, most, or all of the interior of the needle. The one or more stylets may be advanced, actuated, or moved from a retracted position to an advanced position. In the retracted position, the distal end of the one or more stylets may be offset or retracted from the distal end of the one or more needles. The one or more stylets may include one or more notched portions, recesses, cut-outs, or grooves. The one or more notched portions, recesses, cut-outs, or grooves may be located at a distal end, or at a location between the distal and proximal ends of the stylet.

The handle includes various operational components. The first one of the operational components may control motion of the needle sheath and the needle relative to the catheter. A second one of the operational components may control motion of the needle relative to the sheath and the catheter. A third one of the operational components may control motion of the stylet relative to the needle, the sheath and/or the catheter. A fourth one of the operational components may keep the stylet from moving in a proximal direction until the needle is positioned as desired. A fifth one of the operational components may adjust fluid/air pressure at a distal end of the needle, the sheath and/or the catheter.

Figures 1, 2, 3, 4:
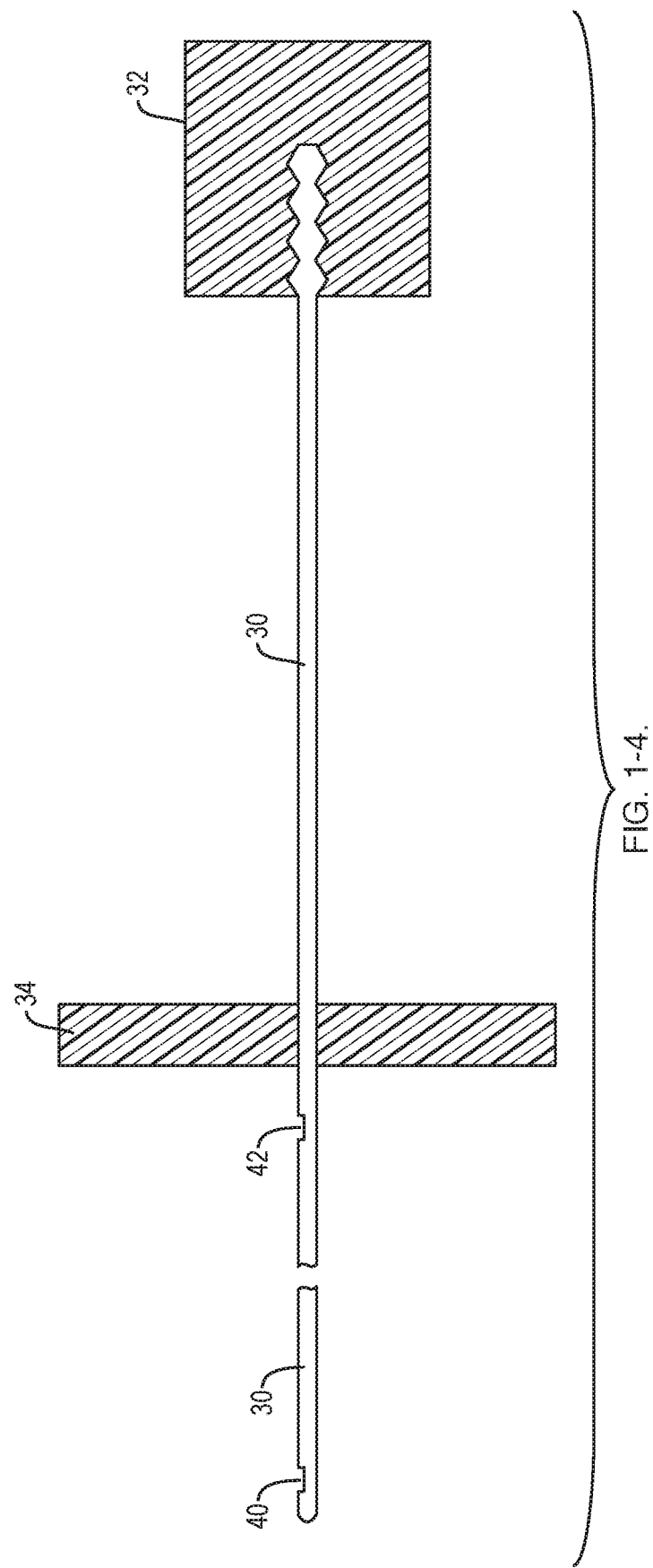
Figure 2:
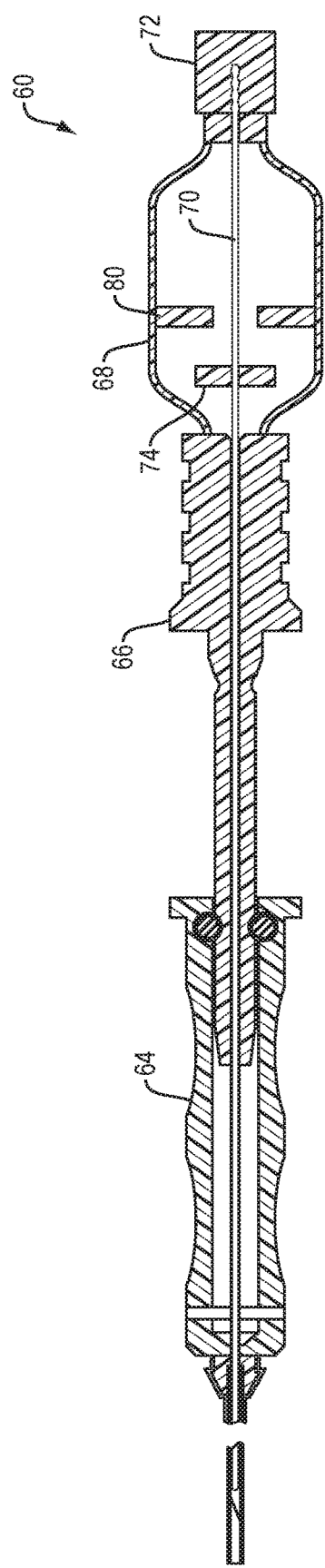
Figure 1:
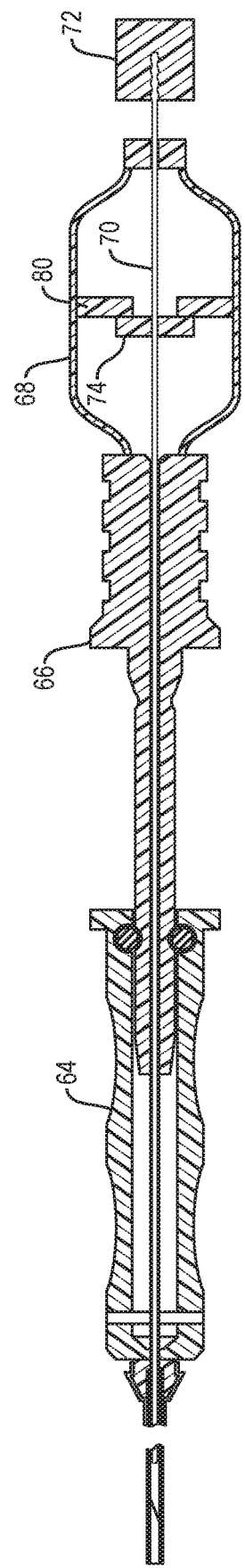
Figures 1, 3:
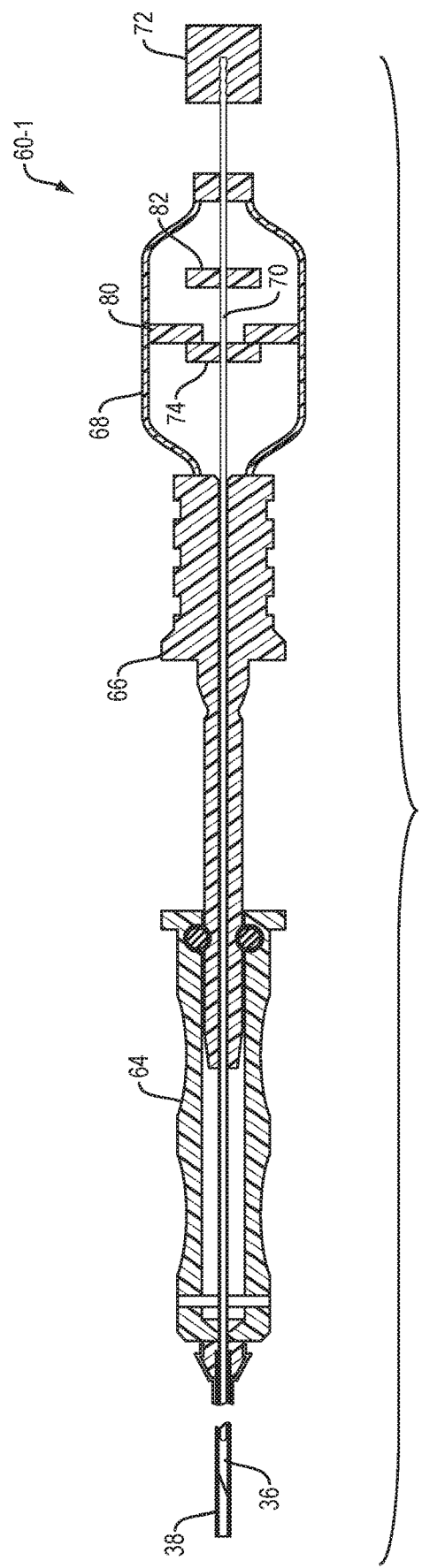
Figures 2, 3:
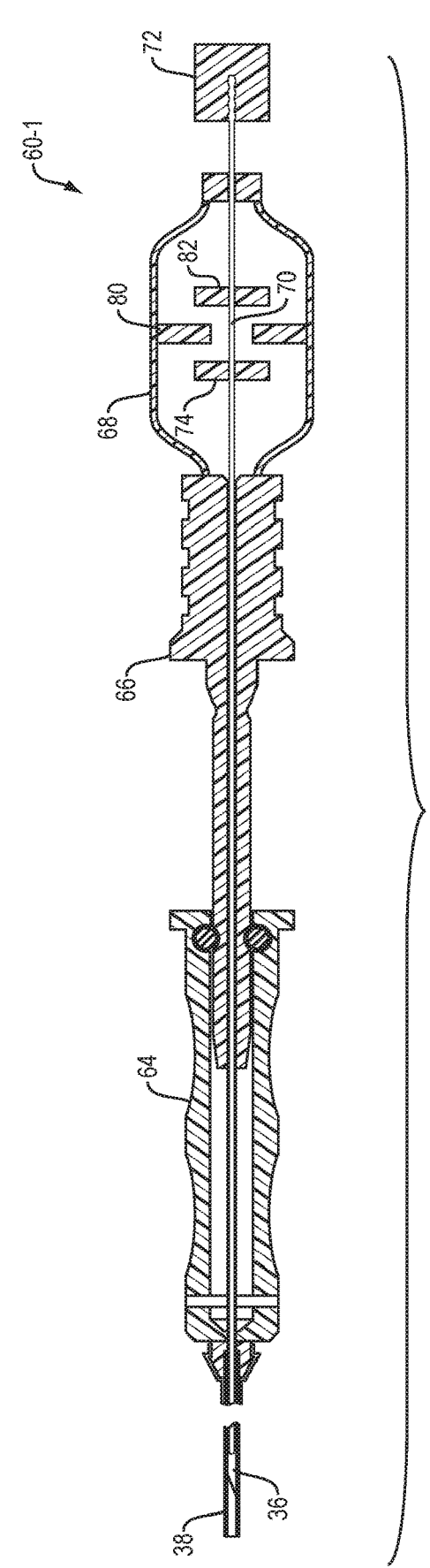
Figure 3:
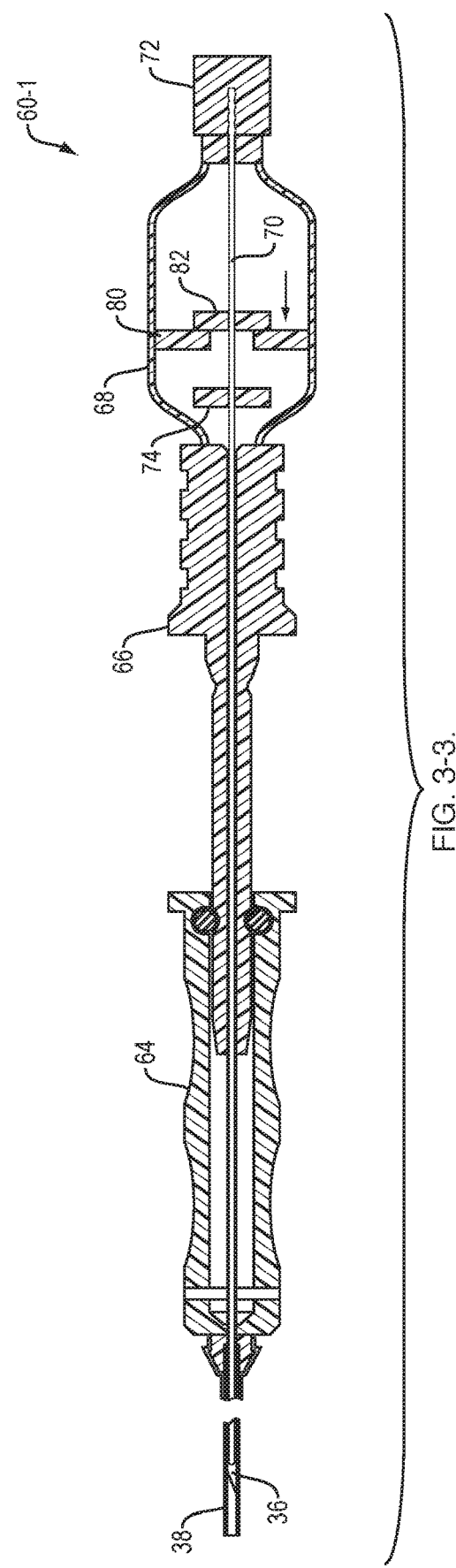

FIG. 1-1 illustrates an example needle aspiration device 20 (e.g., transbronchial needle aspiration (TBNA) device) and FIGS. 1-2 and 1-3 illustrate cross-sectional views of the device 20. The device 20 includes a handle having a handle body 24, a needle actuator 26, a vacuum chamber 28 and a stylet knob 32. The handle body 24 is attached to a proximal end of a sheath 38. The needle actuator 26 includes a shaft portion coupled to a handle portion. The shaft portion is configured to slide within a cavity (i.e., lumen) of the handle body 24. The needle actuator 26 receives and is attached to a proximal end of a needle 36. The stylet knob 32 is attached to a proximal end of a stylet 30. The stylet 30 is received within the vacuum chamber 28 and a lumen of the needle 36. In one embodiment, the vacuum chamber 28 is at least partially transparent for allowing an operator to view the position of the components within. Calibration marks may be applied to the transparent vacuum chamber 28 for providing feedback to the operator about plunger position.

The device 20 may be used for sampling of tissue, for example pulmonary tissue. In some embodiments, the device 20 is configured to be used in thoracoscopic, laparoscopic, transcutaneous, and/or percutaneous procedures. In some such embodiments, the device 20 can be navigated to a nodule or other site of interest within the body via fluoroscopy, tomography or other external visualization techniques. In some configurations, the sheath 38, the needle 36 and the stylet 30 can be inserted into a bronchoscope. Various types of bronchoscopes may be used, including but not limited to the BF-P180 bronchoscope manufactured by Olympus®. Bronchoscopes using ultrasound probes or other visualization devices also can be used, including the EBUS® scope manufactured by Olympus®. The sheath 38 is received within a working channel of the bronchoscope.

In some configurations, the sheath 38 can be inserted into an airway so that the distal end reaches or is placed proximate a region of tissue to be treated and/or sampled. Other configurations are possible. For example, when used relative to other body tissues and/or in other body lumens (e.g., during intestinal or colonoscopy treatments), the device 20 can be loaded into other types of endoscopes. As will be described in greater detail below, the needle 36 is able to pierce through an airway wall or lumen after the sheath 38 is placed proximate a region of targeted tissue, such as a lung nodule, for example but without limitation. In other words, after the sheath 38 passes along one or more airway of the lung, the needle 36 can be used to pierce an airway wall or lumen to gain access to tissue, nodules or the like outside of the airway. In some configurations, the sheath 38 can be passed through an airway and then extend into tissue outside of the airway while remaining within the pleurae.

FIG. 1-4 illustrates the stylet 30 attached the stylet knob 32. In one embodiment, the stylet 30 includes a lumen that extends from the proximal end of the stylet 30 or optionally from a port 42 near the proximal end of the stylet 30 to a port 40 located at or near a distal of the stylet 30. A plunger 34 is fixedly attached to a section of the stylet 30 near the proximal end of the stylet 30. The port 42, if included, is located distal to the plunger 34. As shown in FIG. 1-2, the plunger 34 is positioned along the stylet 30 such that when the stylet knob 32 is fully inserted into the vacuum chamber 28 thus making contact with the end of the vacuum chamber 28, the plunger 34 is positioned near a distal end of the vacuum chamber 28. The plunger 34 may be attached to the stylet 30 using various methods, for example an adhesive or comparable material may be used.

An outer edge or surface of the plunger 34 makes a sealing contact with the inner wall of the vacuum chamber 28 to separate the vacuum chamber 28 into a distal volume of air and a proximal volume of air. As the operator of the device 20 retracts the plunger 30 by gripping the stylet knob 32 and moving the stylet knob 32 and the stylet 30 in a proximal direction, the plunger 34 slides along the inner wall of the vacuum chamber 28. As the plunger 34 slides along the inner wall a seal between the distal volume of air and the proximal volume of air is maintained. The proximal motion of the plunger 34 produces negative or reduced fluid or air pressure within or around the distal end of one of the needle 36, the sheath 38 or the stylet 30 as a result of a pneumatic connection between the distal volume of air in the vacuum chamber 28 and the lumen of the needle 36, the sheath 38 or the stylet 30. This negative or reduced pressure may be similar to that produced by a syringe. The plunger 34 may be made of material similar to that used in a syringe or any material that allows the volume of air located on the proximal side of plunger 34 within the vacuum chamber 28 to remain distinct from the volume of air on the distal side of the plunger 34.

In one embodiment, the stylet knob 32 may be removable to expose a proximal opening of the lumen within the stylet 30 or expose the distal volume of air in the vacuum chamber 28. The stylet knob 32 may also include a cavity that allows for connection between the lumen within the stylet 30 or the distal volume of air in the vacuum chamber 28 to an external device, such as a fluid or gas source. The port 40 at the distal end of the stylet 30 allows for the reception or repulsion of air or fluid into or out of the lumen of the stylet 30 due to what is occurring at the vacuum chamber 28.

In one embodiment, the diameter of the stylet is larger within part of the handle of the device 20 than a portion of the stylet that is received within the needle 36. The stylet tapers from the larger to smaller diameter sections.

In one embodiment, the vacuum chamber 28 has a volume sized that when a plunger is moved proximally the pressure produced at the distal end of the sheath 38, the needle 36 or the stylet 30 is between 2 PSI and 20 PSI. An example of the volume size of the vacuum chamber 28 is between 5*cc* and 30*cc*.

FIGS. 2-1 and 2-2 illustrate cross-sectional views of an example needle aspiration device 60. The device 60 includes a handle having a handle body 64, a needle actuator 66 and a vacuum chamber 68. The handle body 64 is attached to a proximal end of a sheath. The needle actuator 66 includes a shaft portion coupled to a handle portion. The shaft portion is configured to slide within a cavity (i.e., lumen) of the handle body 64. The needle actuator 66 receives and is attached to a proximal end of a needle. The vacuum chamber 68 may be monolithically formed with the needle actuator 66 or may be a separate component that attaches to the needle actuator 66. In one embodiment, the vacuum chamber 68 is at least partially transparent for allowing an operator to view the position of the components within. A stylet knob 72 is attached to a proximal end of a stylet 70. The stylet 70 is received within the needle, the handle body 64, the needle actuator 66 and the vacuum chamber 68.

In one embodiment, the vacuum chamber 68 includes a plunger 80. The plunger 80 makes contact with an inner wall of the vacuum chamber 68. The plunger 80 includes a hole for receiving the stylet 70. A stylet tab 74 is fixedly attached to the stylet 70. When the stylet 70 is received within the handle body 64, the needle actuator 66 and the vacuum chamber 68, the stylet tab 74 is located distal from the plunger 80. When the stylet 70 is in its most proximal position, a gap exists between the plunger 80 and the stylet tab 74. The gap and the hole in the plunger 80 allow for gas(ses) and/or fluid to pass between a distal end of the vacuum chamber 68 and a proximal end of the vacuum chamber 68. The diameter of the stylet tab 74 is less than the diameter of the plunger 80, but is larger than a diameter of the hole in the plunger 80. The stylet tab 74 does not make contact with the inner walls of the vacuum chamber 68.

When the stylet 70 is retracted proximally, the stylet tab 74 makes contact with a portion of a distal surface of the plunger 80. The materials of the plunger 80 and the stylet tab 74 are selected such that when the stylet tab 74 makes contact with the plunger 80 a fluid and/or pneumatic seal is created between the distal portion and the proximal portion of the vacuum chamber 68. As a user further retracts the stylet 70 in the proximal direction, the stylet tab 74 applies a proximal force to the plunger 80, thereby causing the second plunger to move in the proximal direction (see FIG. 2-2). The actions of creating a seal and moving of both the plunger 80 and the stylet tab 74 draws a vacuum (i.e., produces lower or negative pressure) within or around the distal end of one of the needle, the sheath or the stylet 70 due to the distal portion of the vacuum chamber 68 being in fluidic or pneumatic communication with lumen of the needle, the sheath or the stylet 70. This vacuum drawing action may be similar to that of a syringe. The plunger 80 and the stylet tab 74 may be made of material similar to that used in a syringe or any material that allows the volume of air located on the proximal side of the plunger 80 and the stylet tab 74 within the vacuum chamber 68 to remain distinct from the volume of air on the distal side of the plunger 80 and the stylet tab 74.

The stylet knob 72 may be removable to expose a proximal opening of a lumen within the stylet 70. Alternatively or in combination, the stylet knob 72 may include a cavity that allows for connection of the lumen within the stylet 70 to an external device, such as a fluid or air source. A port (e.g., the port 40, FIG. 1-3) at the distal end of the stylet 70 allows for the reception or repulsion of gas(ses) or fluid into or out of the lumen of the stylet 70.

FIGS. 3-1 thru 3-3 illustrate cross-sectional views of an example needle aspiration device 60-1. The device 60-1 is similar to the device 60 of FIGS. 2-1 and 2-2. The device 60-1 includes the plunger 80 and the stylet tab 74 that function similar to that shown in FIGS. 2-1 thru 2-2. In addition, the device 60-1 includes a second stylet tab 82 that may be similar in size to the first stylet tab 74, but is attached to the stylet 70 at a location proximal to the plunger 80.

When the stylet 70 is moved distally, the second stylet tab 82 makes contact with a portion of a proximal surface of the plunger 80. The materials of the first and second stylet tabs 80 and 82 are selected such that when the second stylet tab 82 makes contact with the plunger 80 a fluid and/or pneumatic seal may be created between the distal end and the proximal end of the vacuum chamber 68. As a user further extends the stylet 70 distally, the second stylet tab 82 applies a distal force to the plunger 80, thereby causing the plunger 80 to move in the distal direction. The actions of creating a seal and moving the plunger 80 and the second stylet tab 82 forces gas(ses) or fluid distally through lumen of one of the needle, the sheath or the stylet 70. The second stylet tab 82 may be made of material similar to that used in a syringe or any material that allows the volume of air located on the proximal side of the plunger 80 and the second stylet tab 82 within the vacuum chamber 68 to remain distinct from the volume of air on the distal side of the plunger 80 and the second stylet tab 82.

In one embodiment, the second tab 82 does not form any type of seal with the plunger 80 due to material selection or one or more perforations in the second tab 82. The perforations expose proximal and distal portions of the vacuum chamber 68 to each other via the hole in the plunger 80.

FIGS. 4-1 and 4-2 illustrate cross-sectional views of an example needle aspiration device 88. The device 88 includes a handle having a handle body 64, a needle actuator 66 and a vacuum chamber 68 similar to the device 60 of FIGS. 2-1 and 2-2.

The device 88 further includes a balloon 100 that is positioned along the stylet 30 such that when the stylet 70-1 is fully inserted into the vacuum chamber 68, the balloon 100 is positioned near a distal end of the vacuum chamber 68. A proximal end of the vacuum chamber 68 is sized to allow the stylet 70-1 and the balloon 100 in a deflated state to be removed from the handle.

When the balloon 100 is at least partially inflated, the outer surface of the balloon 100 forms a seal with the inner wall of the vacuum chamber 68. As the operator of the device 88 retracts the balloon 100 by moving the stylet knob 72-1 in a proximal direction, the balloon 100 slides along the inner wall of the vacuum chamber 68. The proximal motion of the balloon 100 draws a vacuum (i.e., negative pressure) within or around the distal end of one of the needle, the sheath or the stylet 70-1. This vacuum drawing action is similar to that of a syringe. The balloon 100 may be made of material similar to that used in a surgical balloons or any material that allows the volume of air located on the proximal side of the balloon 100 within the vacuum chamber 68 to remain distinct from the volume of air on the distal side of the balloon 100, when the balloon 100 is in an inflated state.

The stylet knob 72-1 may be removable to expose a proximal opening of the lumen within the stylet 70-1. A fluidic/pneumatic connection exists between the lumen of the stylet 70-1 and an external device, such as a gas (e.g., air) or fluid supply 90. The lumen extends from the proximal end of the stylet 70-1 or from the cavity of the stylet knob 72-1 to a window 92 in the stylet 70-1. The balloon 100 attaches around the stylet 70-1 at two ends. One end of the balloon 100 is attached aft of the window 92 and the other end of the balloon 100 is attached is forward of the window 92. Air supplied by the air supply 90 exits the window 92 to fill the balloon 100.

FIG. 4-3 illustrates a device 90-1 that is a combined stylet knob and air supply mechanism. The device 90-1 includes a small finger actuated pump 114 and a one-way check valve 112 with a release mechanism 116 for controlling pneumatic communication between the pump 114 and the balloon 100 on the stylet 70-1. The device 90-1 is attachable to the stylet 70-1. The pump 114 may be molded from rubber such as butyl rubber or a latex rubber to form a rubber bulb. The pump 114 may also be a molded urethane or other material having good memory characteristics. At one end of the device 90-1 is a pump valve 110 that prevents air from passing from the pump 114 to the atmosphere while allowing air to pass into the pump 114. At the other end of the device 90-1 is the one-way valve 112, which enables air to be forced into the balloon 100 via the stylet lumen upon application of pressure to the pump 114. The one-way check valve 112 prevents air from traveling from the balloon 100 to the pump 114. Therefore, the balloon 100 is pumped up simply by depressing the pump 114 repeatedly until the balloon 100 has reached a desired pressure. The device 90-1 includes a release mechanism 116 that is a depressible valve used to release air from the balloon 100 according to the desires of the user. A housing of the device 90-1 includes the check valves 110 and 112 and the release mechanism 116 and houses the pump 114.

Embodiments

A. A device comprising: a sheath having a distal end and a proximal end; a medical device having a distal end and a proximal end, the medical device comprising a lumen; a stylet having a distal end and a proximal end; a handle comprising: a base portion connected to the proximal end of the sheath, the base portion comprising a lumen; an actuator connected to the proximal end of the medical device, the actuator comprising: a shaft portion configured to slide within the lumen of the base portion; and a handle portion connected to the shaft portion, wherein at least one of the shaft portion or the handle portion is connected to the proximal end of the medical device; and a chamber portion connected to the actuator, the chamber portion comprising a volume of space configured to volumetrically connect to at least one of the lumen of the medical device or the sheath; and a plunger device configured to slide within the chamber portion and configured to pneumatically or hydraulically isolate a proximal portion of the volume of space from a distal portion of the volume of space.

B. The device of A, wherein the plunger device comprises a plunger that is attached to the stylet at one or more locations and makes a seal with an interior wall of the chamber portion.

C. The device of A, wherein the plunger device comprises: a plunger with a hole having a diameter dimension greater than a diameter dimension of the stylet; and a tab attached to the stylet, the tab being located on a distal side of the plunger when the stylet is received through the hole within the chamber portion.

D. The device of C, wherein the stylet further comprising: a lumen; a distal port; and a proximal port, wherein proximal motion of the stylet causes reduced pressure at the distal end of at least one of the medical device, the sheath or the stylet due to the plunger moving as a result of the tab applying a proximal force to the plunger.

E. The device of C, wherein at least one of a pneumatic or fluidic communication exists between a proximal portion of the volume of space and a distal portion of the volume of space when the tab is not in contact with the plunger.

F. The device of C, wherein the plunger device comprises a second tab attached to the stylet, the second tab is located on a proximal side of the plunger when the stylet is received through the hole within the chamber portion.

G. The device of F, wherein at least one of air or fluid communication exists between a proximal portion of the volume of space and a distal portion of the volume of space when the first tab and the second tab are not in contact with the plunger.

H. The device of F, wherein the stylet further comprising: a lumen; a distal port; and a proximal port, wherein distal motion of the stylet causes increased pressure at the distal end of at least one of the medical device, the sheath or the stylet due to the plunger moving as a result of the second tab applying a distal force to the plunger.

I. The device of A, wherein the stylet comprises a port and a lumen that extends from a proximal end of the stylet to the port, wherein the plunger device comprises an inflatable balloon attached to the stylet around the port, the device further comprising at least one of a gas or a fluid source configured to supply a gas or a fluid into the inflatable balloon via the stylet lumen and the port, wherein when the inflatable balloon is in an inflated state, a portion of an outer surface of the balloon makes at least one of a pneumatic or fluidic seal with an inner wall of the chamber portion.

J. The device of I, wherein proximal motion of the stylet causes reduced pressure at the distal end of at least one of the medical device, the sheath or the stylet due to the inflatable balloon in the inflated state moving proximally.

K. The device of I, wherein the gas or the fluid source comprises a pump device directly connected to the proximal end of the stylet.

L. The device of K, wherein the pump comprises: a bulb pump; a first check valve connected between the bulb pump and surrounding environment; and a second check valve connected between the bulb pump and the balloon and the stylet lumen.

M. The device of L, wherein the pump further comprises a release valve configured to release air pressure in the balloon.

N. The device of A, wherein the medical device comprises a needle.

O. A method comprising: moving a stylet in a proximal direction relative to a handle device and at least one of a sheath and a medical device, wherein the handle device comprises components connected to proximal ends of the sheath, the medical device and the stylet; moving a plunger device located within a chamber of the handle device based on the moving of the stylet, wherein the moving of the plunger device occurs in a proximal direction relative to the chamber, wherein the plunger device provides a separation between a first volume of space within the chamber and a second volume of space within the chamber, the first volume of space being distal from the plunger device and the second volume the space being proximal from the plunger device; and reducing pressure at a distal end of at least one of the medical device, the sheath or the stylet based on the moving of the plunger device.

P. The method of O, further comprising: receiving a sample of tissue at the distal end of at least one of the sheath, the medical device or the stylet based on the reduced pressure.

Q. The method of O, wherein the plunger device comprises a first tab attached to the stylet and a plunger configured to seal with an inner wall of the chamber, wherein moving the plunger device further comprises: moving the first tab into contact with the plunger; and simultaneously moving the first tab and the plunger in the proximal direction.

R. The method of Q, further comprising: passing fluid from the second volume of space to the first volume of space when the first tab is not in contact with the plunger.

S. The method of Q, wherein the plunger device further comprises a second tab attached to the stylet proximal from the plunger, further comprising: moving the second tab into contact with the plunger; and simultaneously moving the second tab and the plunger in the distal direction.

T. The method of O, wherein the plunger device comprises: a balloon attached to the stylet at first and second locations; a first port located on the stylet between the first and second locations; a second port located at or near a proximal end of the stylet; and a lumen configured to connect the first and second ports, wherein moving the plunger device further comprises: inflating the balloon using an air source coupled to the second port; and moving the balloon in the proximal direction.

Although this invention has been disclosed in the context of certain embodiments and examples, those skilled in the art will understand that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It should be understood that various features and aspects of the disclosed embodiments can be combined with, or substituted for, one another in order to form varying modes or embodiments of the disclosed invention. Thus, it is intended that the scope of the present invention herein disclosed should not be limited by the particular disclosed embodiments described above.

What is claimed is:
1. A device comprising:
 a sheath having a distal end and a proximal end;
 a medical device having a distal end and a proximal end, the medical device comprising a lumen;
 a stylet having a distal end and a proximal end;
 a handle comprising: a base portion connected to the proximal end of the sheath, the base portion comprising a lumen;
 an actuator connected to the proximal end of the medical device, the actuator comprising:
 a shaft portion received within the lumen of the base portion, the shaft portion configured to slide and move within the lumen of the base portion;
 and a handle portion connected to the shaft portion, wherein at least one of the shaft portion or the handle portion is connected to the proximal end of the medical device;

and a chamber portion connected to the actuator, the chamber portion comprising a volume of space configured to volumetrically connect to at least one of the lumen of the medical device or the sheath;

and a plunger device configured to be received within the chamber portion, configured to pneumatically isolate a proximal portion of the volume of space from a distal portion of the volume of space within the chamber portion, and configured to be at least partially connected to the proximal end of the stylet, wherein the stylet is configured to apply a proximal force to the plunger via a proximal motion of the stylet thereby causing a proximal motion of the plunger resulting in reduced pressure at the distal end of at least one of the medical device, the sheath or the stylet.

2. The device of claim 1, wherein the plunger device comprises a plunger that is attached to the stylet at one or more locations and makes a seal with an interior wall of the chamber portion.

3. The device of claim 1, wherein the plunger device comprises:
a plunger with a hole having a diameter dimension greater than a diameter dimension of the stylet; and
a tab attached to the stylet, the tab being located on a distal side of the plunger when the stylet is received through the hole within the chamber portion.

4. The device of claim 3, wherein the stylet further comprises: a lumen; a distal port; and a proximal port, wherein proximal motion of the stylet is configured to cause, the plunger to move as a result of the tab applying a proximal force to the plunger.

5. The device of claim 3, wherein at least one of pneumatic communication or fluidic communication exists between a proximal portion of the volume of space and a distal portion of the volume of space when the tab is not in contact with the plunger.

6. The device of claim 3, wherein the plunger device comprises a second tab attached to the stylet, the second tab is located on a proximal side of the plunger when the stylet is received through the hole within the chamber portion.

7. The device of claim 6, wherein at least one of pneumatic communication or fluidic communication exists between a proximal portion of the volume of space and a distal portion of the volume of space when the first tab and the second tab are not in contact with the plunger.

8. The device of claim 6, wherein the stylet further comprises: a lumen; a distal port; and a proximal port, wherein distal motion of the stylet is configured to cause increased pressure at the distal end of at least one of the medical device, the sheath or the stylet due to the plunger moving as a result of the second tab applying a distal force to the plunger.

9. The device of claim 1, wherein the stylet comprises a port and a lumen that extends from a proximal end of the stylet to the port, wherein the plunger device comprises an inflatable balloon attached to the stylet around the port, the device further comprising at least one of a gas or a fluid source configured to supply a gas or a fluid into the inflatable balloon via the stylet lumen and the port, wherein when the inflatable balloon is in an inflated state, a portion of an outer surface of the balloon makes at least one of a pneumatic or fluidic seal with an inner wall of the chamber portion.

10. The device of claim 9, wherein proximal motion of the stylet is configured to cause reduced pressure at the distal end of at least one of the medical device, the sheath or the stylet due to the inflatable balloon in the inflated state moving proximally.

11. The device of claim 9, wherein the gas or the fluid source comprises a pump device directly connected to the proximal end of the stylet.

12. The device of claim 11, wherein the pump device comprises:
a bulb pump;
a first check valve connected between the bulb pump and a surrounding environment; and
a second check valve connected between the bulb pump and the stylet lumen.

13. The device of claim 12, wherein the pump further comprises a release valve configured to release air pressure in the balloon.

14. The device of claim 1, wherein the medical device comprises a needle.

15. A method comprising:
moving a stylet in a proximal direction relative to a handle device and at least one of a sheath and a medical device, wherein the handle device comprises components connected to a proximal end of the sheath, a proximal end of the medical device, and a proximal end of the stylet, wherein the stylet applies a proximal force to
a plunger device located within a chamber of the handle device, wherein the moving of the plunger device occurs in a proximal direction relative to the chamber, wherein the plunger device provides a separation between a first volume of space within the chamber and a second volume of space within the chamber, the first volume of space being distal from the plunger device and the second volume the space being proximal from the plunger device; and
reducing pressure at a distal end of at least one of the medical device, the sheath or the stylet based on proximal motion of the plunger device.

16. The method of claim 15, further comprising: receiving a sample of tissue at the distal end of at least one of the sheath, the medical device or the stylet based on the reduced pressure.

17. The method of claim 15, wherein the plunger device comprises a first tab attached to the stylet and a plunger configured to seal with an inner wall of the chamber,
wherein moving the plunger device further comprises:
moving the first tab into contact with the plunger; and
simultaneously moving the first tab and the plunger in the proximal direction.

18. The method of claim 17, further comprising:
passing a fluid from the second volume of space to the first volume of space when the first tab is not in contact with the plunger.

19. The method of claim 17, wherein the plunger device further comprises a second tab attached to the stylet proximal from the plunger,
the method further comprising:
moving the second tab into contact with the plunger; and
simultaneously moving the second tab and the plunger in the distal direction.

20. The method of claim 15, wherein the plunger device comprises:
a balloon attached to the stylet at first and second locations;
a first port located on the stylet between the first and second locations;
a second port located at or near a proximal end of the stylet; and
a lumen configured to connect the first port and the second port,
wherein moving the plunger device further comprises:

inflating the balloon using an air source coupled to the second port; and moving the balloon in the proximal direction.

\* \* \* \* \*